United States Patent [19]

Huey

[11] Plant 4,475

[45] Nov. 6, 1979

[54] *ACALYPHA WILKESIANA* 'DALLAS'

[75] Inventor: G. Philip Huey, Dallas, Tex.

[73] Assignee: City of Dallas, Dallas, Tex.

[21] Appl. No.: 926,944

[22] Filed: Jul. 20, 1978

[51] Int. Cl.[2] ..... A01H 5/12

[52] U.S. Cl. ..... Plt./88

[58] Field of Search ..... Plt./88

[56] References Cited

PUBLICATIONS

Tropica, Graf, 1978, Roehrs Co., E. Rutherford, N.J., pp. 409 and 931.

*Primary Examiner*—Robert E. Bagwill

[57] ABSTRACT

*Acalypha wilkesiana* 'Dallas': leaves ovate—slightly serrated, mottled and streaked half yellow and green, occasionally streaked white, with inconspicuous pale pink staminate flowers. Tropical.

2 Drawing Figures

1

DESCRIPTION

The leaves are mottled and best described as streaked half yellow and half green, occasionally streaked white, corresponding to Royal Horticultural Color Chart Codes 141B, 144A, 150D, 154B and 155A. *Acalypha wilkesiana* 'Dallas' was discovered as a bud sport during the summer of 1976 on *Acalypha wilkesiana* that was planted at the Marsalis Zoo located in Dallas, Tex. The cultivar has been successfully propagated by stem cuttings since its discovery. It is a unique cultivar because of its yellow and green mottled leaves which differs from the red mottled leaves of the species. A distinct

2 quality that 'Dallas' Acalypha displays over the species is its preference to shade and half sun, Acalypha ordinarily being a sun-loving plant. The cultivar suffers leaf burn and necrosis in full sun. The new cultivar is otherwise similar to the parent plant. FIG. 1 depicts the cultivar. FIG. 2 is a detail of one leaf depicting the various shades of color. Both figures show the unique colors of this cultivar.

I claim:

1. A new and distinct variety of *Acalypha wilkesiana*, substantially as shown and described, characterized by its predominantly yellow and green foliage.

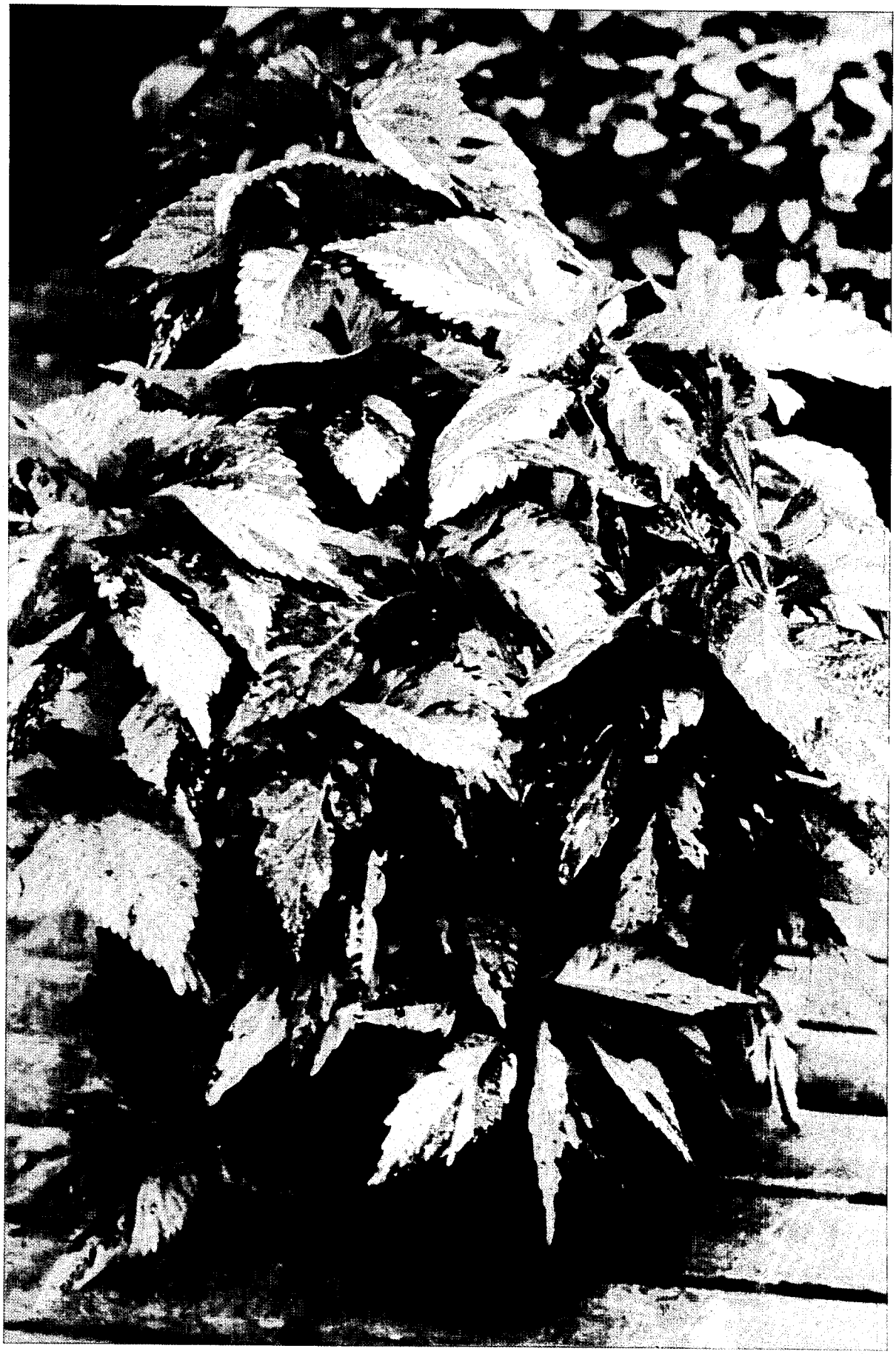

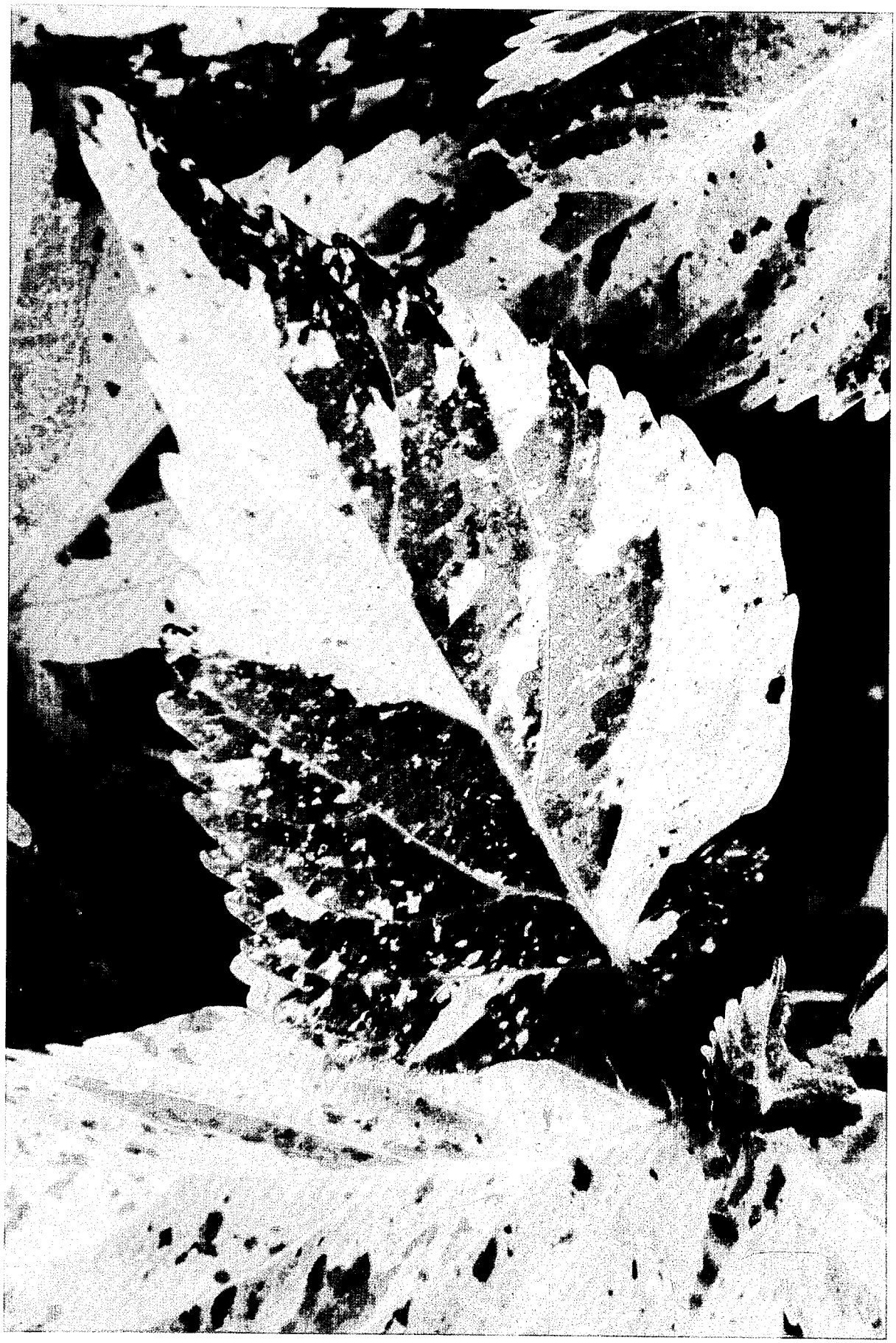

* * * * *